United States Patent
Smethers et al.

[11] Patent Number: 6,045,549
[45] Date of Patent: Apr. 4, 2000

[54] TISSUE ABLATION APPARATUS AND DEVICE FOR USE THEREIN AND METHOD

[75] Inventors: Rick T. Smethers, Fremont; Benjamin T. Nordell, II, Menlo Park, both of Calif.

[73] Assignee: Somnus Medical Technologies, Inc., Sunnyvale, Calif.

[21] Appl. No.: 08/941,401

[22] Filed: Sep. 30, 1997

[51] Int. Cl.$^7$ .................................................. A61B 17/39
[52] U.S. Cl. .............................................. 606/39; 604/22
[58] Field of Search ................................. 606/32, 33, 34, 606/39, 40, 41, 44, 198; 604/22

[56] References Cited

U.S. PATENT DOCUMENTS

| | | | |
|---|---|---|---|
| 5,549,644 | 8/1996 | Lundquist et al. | 604/22 |
| 5,601,591 | 2/1997 | Edwards et al. | 606/198 |
| 5,741,225 | 4/1998 | Lax et al. | 604/22 |

*Primary Examiner*—George Manuel
*Attorney, Agent, or Firm*—Flehr Hohbach Test Albritton & Herbert LLP

[57] ABSTRACT

A tissue ablation apparatus for minimally invasive treatment for disorders of the upper airway by the treatment of soft tissues in the upper airway comprising a hand-held device adapted to be held by the human hand. Radio frequency energy is delivered to the hand-held device. The hand-held device comprises a housing having a handle portion adapted to be grasped by the human hand and a probe portion. At least one guide tube is mounted in the probe portion and has a bore extending therethrough. A carrier block is slidably mounted in the housing relative to the guide tube. At least one needle assembly is mounted in the carrier block assembly and is movable with the carrier block assembly. The at least one needle assembly extends distally of the carrier block and is slidably disposed in the at least one guide tube. A slider is mounted on the housing exterior of the housing for slidable movement longitudinally of the housing and is adapted to be grasped by the thumb of the hand holding the housing. The slider is connected to the carrier block whereby when the slider is moved distally, the carrier block with the needle assembly is moved in the guide tube distally of the guide tube for entrance into the soft tissue.

16 Claims, 3 Drawing Sheets

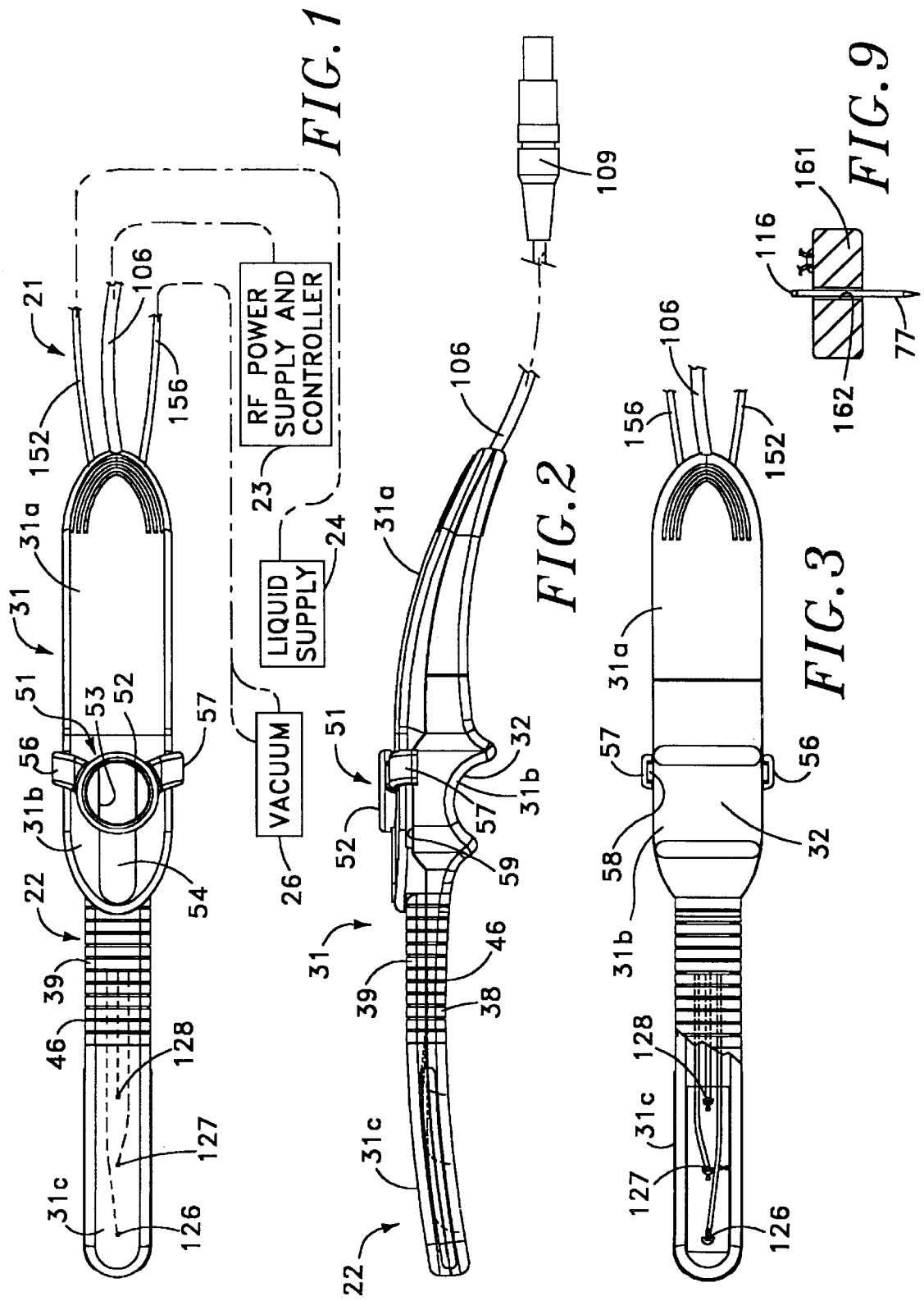

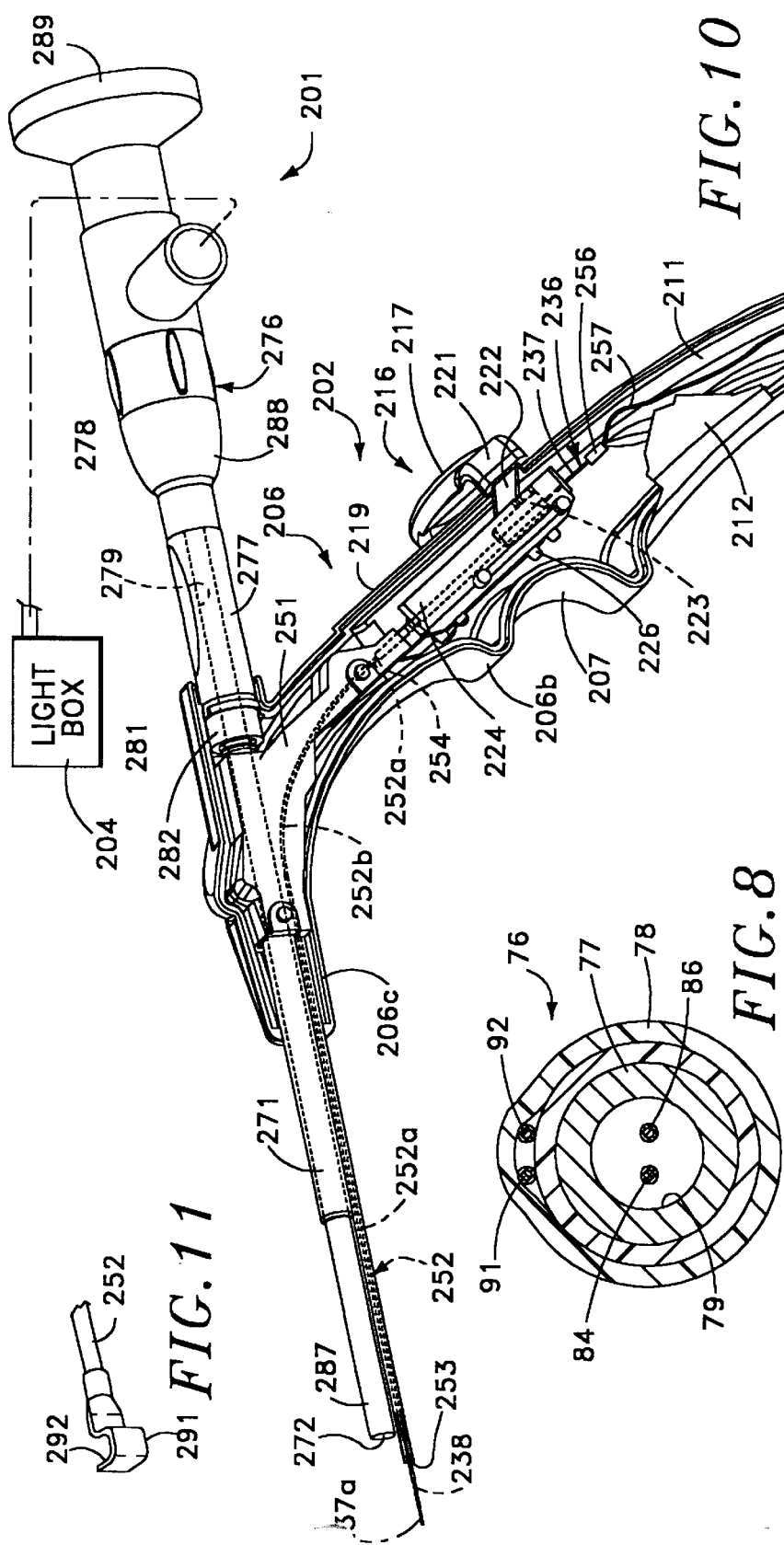
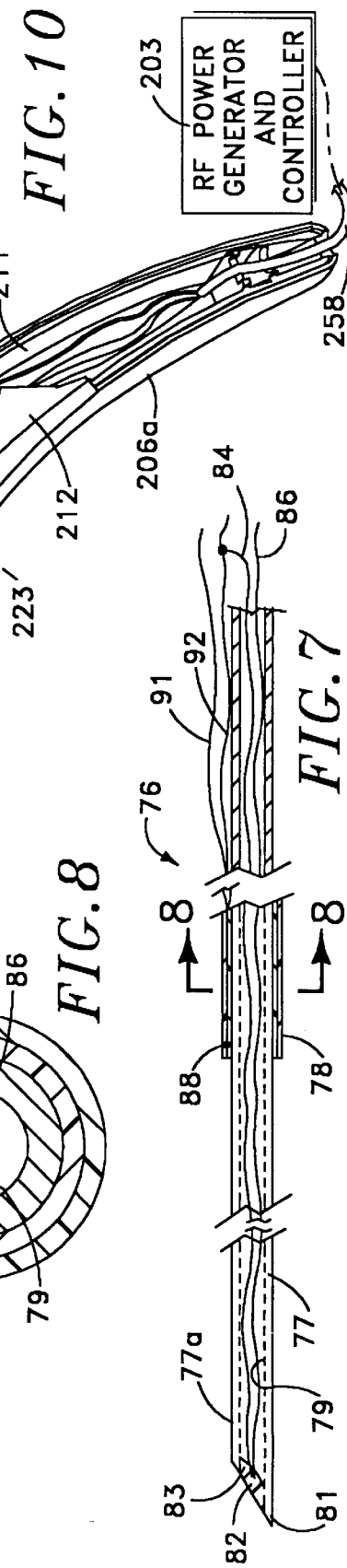

TISSUE ABLATION APPARATUS AND DEVICE FOR USE THEREIN AND METHOD

This invention relates to a tissue ablation apparatus and device for use therein and method and more particularly to a tissue ablation apparatus and device for use therein and method for minimally invasive treatment of disorders of the upper airway of a patient, including snoring and obstructive sleep apnea, enlarged turbinates, tonsils and other upper airway obstructions.

Tissue ablation devices and methods have heretofore been provided. However, they have often not been designed to meet other applications, as for example treatment of disorders of the upper airway. There is therefore a need for a new and improved tissue ablation apparatus and method which are designed to perform specific tissue ablation procedures on specific tissues.

In general, it is an object of the present invention to provide a tissue ablation device and method which can be utilized for performing specific tissue ablation procedures.

Another object of the invention is to provide a device for use in the tissue ablation apparatus in which the surgeon performing the procedure can firmly grip the device in one hand while performing the procedure.

Another object of the invention is to provide a tissue ablation device of the above character which has a high perceived value.

Another object of the invention is to provide a device of the above character which has good ergonomics.

Another object of the invention is to provide a device which is designed for performing procedures on specific portions of the human body and the tissue associated therewith.

Another object of the invention is to provide a device of the above character which can be manufactured economically.

Additional objects and features of the invention will appear from the following description in which the preferred embodiments are set forth in detail in conjunction with the accompanying drawings.

FIG. 1 is a top plan view of a tissue ablation apparatus incorporating the present invention and particularly showing a device for use in the same.

FIG. 2 is a side elevational view of the device shown in FIG. 1.

FIG. 3 is a bottom plan view of the device shown in FIG. 1.

FIG. 7 is an enlarged sectional view of the distal extremity of a needle assembly utilized in the device shown in FIGS. 2–6.

FIG. 8 is a cross-sectional view taken along the line 8—8 of FIG. 7.

FIG. 9 is a cross-sectional view similar to FIG. 6 showing the use of a Peltier device for cooling and heating.

FIG. 10 is an isometric view of another device incorporating the present invention for use in the treatment of soft tissue in the upper airway of a patient with a substantial portion of a side cover removed.

FIG. 11 is a partial side-elevational view of the distal extremity of another device incorporating the present invention particularly adapted for treatment of the uvula.

Figure 4:
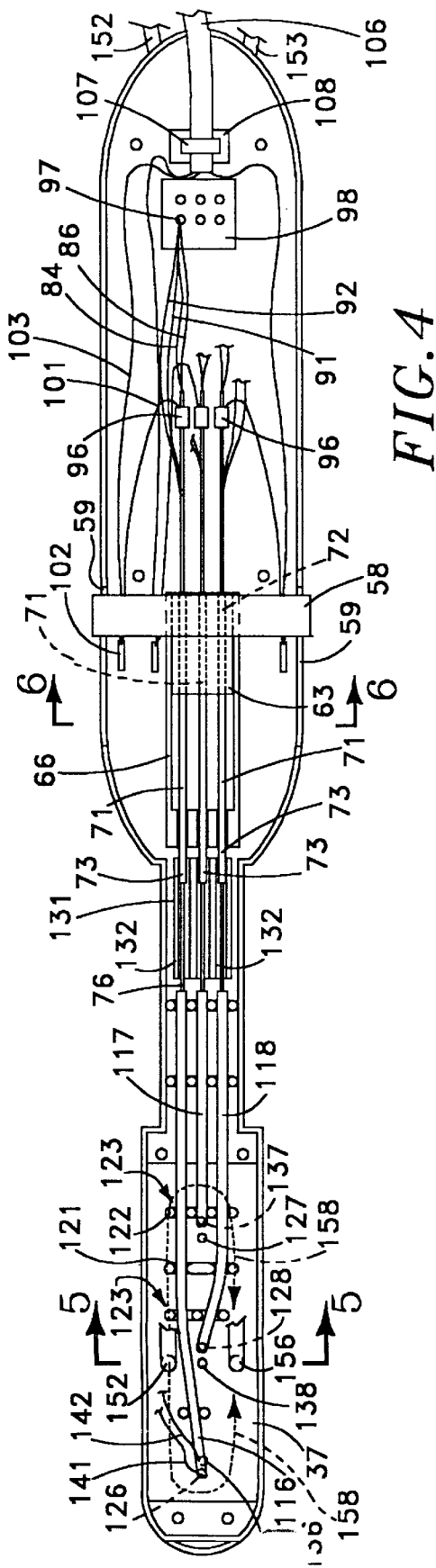
FIG. 4 is a top plan view of the device shown in FIG. 1 with the top cover removed.
Figure 6:
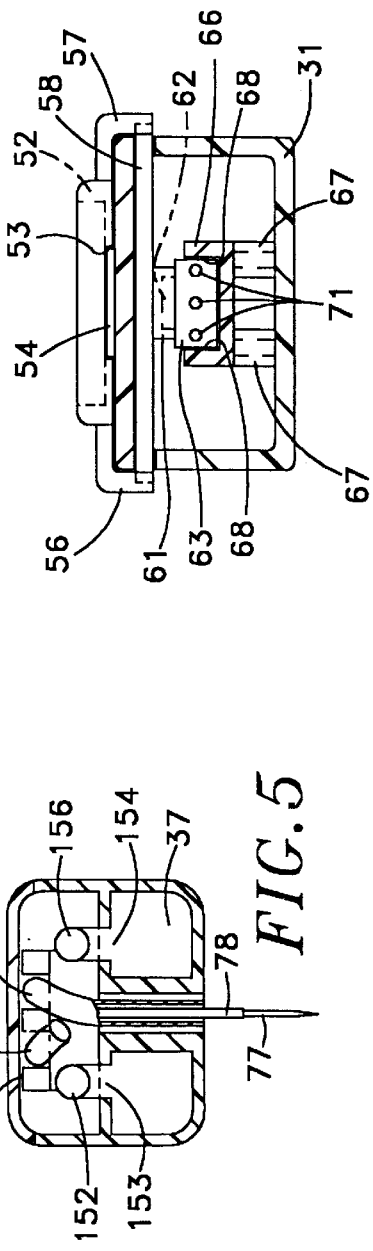
FIG. 6 is a cross-sectional view taken along the line 6—6 of FIG. 4.
Figure 5:
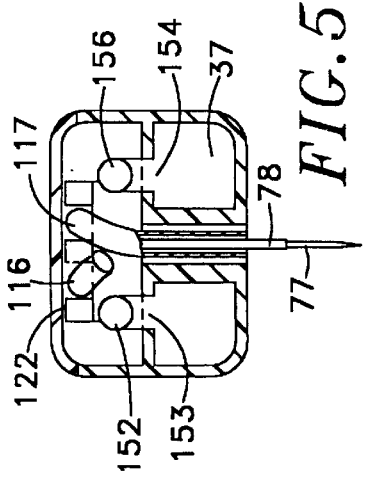
FIG. 5 is a cross-sectional view taken along the line 5—5 of FIG. 4.

In general, the tissue ablation apparatus is for the minimally invasive treatment of disorders of the upper airway of a patient by the treatment of soft tissues in the upper airway. The apparatus comprises a hand-held device adapted to be held by the human hand and means for delivering radio frequency energy to the hand-held device. The hand-held device comprises a housing having a handle portion adapted to be grasped by the human hand and a probe portion. A guide tube is carried by the probe portion and has a bore extending therethrough. A carrier block is slidably mounted in the housing relative to the guide tube. A needle assembly is mounted in the carrier block assembly and is movable with the carrier block assembly. The needle assembly extends distally of the carrier block and is slidably disposed in the guide tube. A slider is mounted on the housing exterior of the housing for slidable movement longitudinally of the housing and has a portion thereof adapted to be grasped by the thumb of the hand holding the housing. Means is provided which connects the slider to the carrier block whereby when the slider is moved, the carrier block with the needle assembly is moved in the guide tube.

More in particular, the tissue ablation apparatus and device for use in the same and the method to be described therewith is shown in FIGS. 1 through 6. The tissue ablation apparatus 21 consists of a tissue ablation device 22 and a radio frequency power supply and controller 23, a liquid supply 24 and a vacuum supply 26 all of which are connected to the device 22 as shown.

The device 22 consists of a housing 31 which is provided with a proximal handle portion 31a which is sized so that it is adapted to be grasped by the hand and in particular by the palm of the hand and the three fingers of the hand other than the index finger and the thumb of the hand. It is also provided with an intermediate portion 31b which has a slot 32 therein that is adapted to be grasped by the index finger of the same hand holding the handle portion 31a. The housing 31 is also provided with an operative probe portion 31c which in the case of the present configuration of the invention is a tongue depression portion 31c which is distal of the intermediate portion 31b. As can be seen, both portions 31a and 31c have a slight curvature to adapt themselves to the particular application of the device 22.

The housing 31 is formed of a suitable material such as a plastic of a suitable type such as a polycarbonate. The housing 31 is formed into a lower part 34 and a top part 36. The upper and lower parts 34 and 36 form a shell-like enclosure providing an enclosed space 37 for the components hereinafter described. The device 22 is provided with a conventional tongue and groove construction (not shown) which are nested or mated together and then fastened together by a suitable means such as an adhesive (not shown) to retain the lower and upper parts 34 and 36 in a unitary assembly.

Bite pads 38 and 39 are provided on the upper and lower parts 34 and 36 adjacent the proximal portions of the tongue depressor portion 31c of the device 22. These bite pads are formed of a low durometer material as for example 40–80A durometer and preferably approximately 50A durometer. One satisfactory material has been found to be Santaprene which is a moldable polymer having approximately a 50A durometer. The bite pads 38 and 39 are molded in the desired shape and are fitted into cutouts 41 and 42 provided in the upper and lower parts 34 and 36. The cutouts are provided with inward extending protrusions 43 which seat in holes 44 provided in the upper and lower parts 34 and 36. In addition if desired, an adhesive (not shown) can be provided for securing the bite pads 38 and 39 to the upper and lower parts 34 and 36. The bite pads 38 and 39 are provided with a plurality of encircling spaced apart recesses 46 spaced a suitable distance apart as for example 20 mm extending the length of the same to aid the bite pads 38 and 39 in serving their function and to facilitate deformation of the bite pads when they are gripped by the teeth of the patient during a procedure hereinafter described.

A slider 51 is slidably mounted on the exterior of the housing 31 in a manner hereinafter described which is adapted to be grasped by the thumb of the hand holding the device. The slider consists of a ring 52 which has a diameter which is sized so as adapted to receive the thumb of the human hand. The slider 51 is provided with an elongate slot or recess 53 which receives a longitudinally and upwardly extending protrusion 54 extending longitudinally of the upper part 36 of the handle portion 31a to guide the slider 51 as it is moved longitudinally of the housing 31. The slider 51 is also provided with rearwardly and downwardly depending side arms 56 and 57 which engage and are connected to opposite ends of a T-shaped bar 58 extending through longitudinal slots 59 provided on opposite sides of the housing 31. The T-shaped bar 58 which serves as a cross member is provided with a rectangular boss 61 which fits over a rectangular protrusion of a rectangular carrier block 63. The carrier block 63 is seated within a sliding block guide assembly 66. This sliding block guide assembly 66 is mounted upon posts 67 forming a part of the housing 31. The side margins of the carrier block 63 are received by the guide block assembly 66 which permits longitudinal movement of the carrier block 63 longitudinally of the housing 31.

A plurality of carrier tubes 71, in this case three carrier tubes are mounted in the carrier block 63 and are spaced apart in a horizontal plane and have proximal extremities 72 which extend just proximally of the carrier block 63 and have distal extremities 73 which extend substantially beyond the carrier block 63.

A needle assembly 76 (see FIG. 7) is mounted in each of the carrier tubes 71 and consists of a needle 77 and insulating sleeve 78. The needle can be formed of a suitable material such a stainless steel or Nitinol and is provided with a bore 79 extending therethrough and is provided with a sharpened tip 81. A first thermocouple 82 is mounted in epoxy 83 in the tip 81 and has insulated conductive wires 84 and 86 extending proximally therefrom through the bore 79. The distal extremity 77a of the needle 77 is bare or uncovered and forms the active region for the needle and has a suitable length as for example 5 to 10 μm and preferably a length of approximately 7.5 μm. A second thermocouple 88 is disposed at the termination of the insulating sleeve 78 adjacent the bare portion 77a of the needle 77. The second thermocouple 88 is connected to insulated conductive wires 91 and 92 which extend along the length of the insulation and exit from the insulating sleeve 78 at a point just distal of a connector 96 mounted on the needle 77. The wires 91 and 92 extend into a mounting block 97 and are soldered to mounting posts 97 on a mounting block 98. The wires 84 and 86 extend through the connector 96 and are also connected to mounting posts 97 provided on the mounting block 98. As shown, the wires 84 and 86 and 91 and 92 are provided with slack so as to permit longitudinal movement of the needle assemblies 76 as hereinafter described. An insulated conductor 101 is connected to the connector 96 and is provided for supplying for supplying radio frequency energy to the connector 96. It is bonded to the housing at point 102 and is connected by solder to another connector 103 which extends around the mounting block 98 and is connected into a cable 106 extending out of the housing 31. The cable 106 is provided with an enlargement 107 that is seated within an upstanding receptacle 108 formed as a part of the lower part 36 of the housing 31 and serves to prevent tensioning forces from being applied to the wires extending into the cable 106 from the mounting block 98.

As shown in FIG. 4, three needle assemblies 76 are provided which are mounted in the carrier tubes 71 and are fixed therein by suitable means such as an adhesive (not shown). The distal extremities of the needle assemblies 76 are slidably mounted in three separate guide tubes 116, 117 and 118 that are pre-bent to have a predetermined configuration. The guide tubes 116, 117 and 188 are disposed in a plurality of longitudinally extending trackways 121 which are formed by a plurality of upstanding pins 122 formed integral with the housing 31 and which are spaced apart transversely of the longitudinal axis of the housing 31. The pins 122 are arranged in a plurality of rows 123 which are spaced apart longitudinally and extend just proximally of the proximalmost row 123.

The lower part 36 of the housing 31 is provided with three longitudinally aligned holes 126, 127 and 128 which are spaced apart longitudinally of the tongue depressor portion 31c. The guide tube 116 is preformed so that it extends through the distalmost hole 126. The guide tube 117 extends into the proximalmost hole 127 and the guide tube 118 extends through the intermediate hole 128. By such an arrangement of the tubes 116, 117 and 118 it can be seen that their three bend shapes form guide paths which lie in a horizonal plane into the three holes which are spaced apart longitudinally but are aligned longitudinally without the necessity of any crossover of the guide tubes 116, 117 and 118. The guide tubes 116, 117 and 118 can be secured between the upstanding pins 122 by a suitable means such as an adhesive (not shown). The distal extremities of the guide tubes 116, 117 and 118 are provided with preformed bends so that the bores therein (not shown) in the guide tubes extend in a direction perpendicular to the plane of the lower part 34. The proximalmost ends of the guide tubes 116, 117 and 118 extend just proximal of the proximalmost row 123 of the pins 122 and have their bores aligned with three transversely spaced-apart trackways 131 formed by a plurality of longitudinally extending upstanding ribs 132 which are spaced apart transversely. These trackways 131 receive the needle assemblies 76 carried by the carrier tubes 71 and serve to guide the needle assemblies 76 as they travel through the guide tubes 116, 117 and 118.

Although only three needle assemblies 76 are shown in FIG. 4, it should be appreciated that more needle assemblies can be provided when desired, as for example, six. It also should be appreciated that although the three needle assemblies are in line, that the three or more needle assemblies 76 can be arranged in different patterns if desired. For example, a diamond-shaped or cross pattern can be used depending on the region of the tongue it is desired to treat.

Third thermocouple means is provided for each of the needle assemblies 76. Thus there are provided third thermocouples 136, 137 and 138 which are mounted in holes 139 just proximal of the holes 126, 127 and 128 and which are secured therein by suitable means such as an adhesive. The third thermocouples are disposed so that they are substantially flush with the exterior surface of the lower part 36 of the housing 31. The third thermocouples 136, 137 and 138 are each provided with insulating conductive wires 141 and 142 that extend proximally of the lower part 34 of the housing 31 and are also connected onto posts 97 provided in the mounting block 98 and from there are connected by conductors (not shown) into the cable 106.

Means is provided for providing surface temperature stabilization for the exterior surface of the lower part 34 of the housing 31 forming the tongue depressor portion 31c and consists of means for supplying a surface temperature stabilization liquid into the space or cavity 37 provided in the tongue depression portion 31c between the lower part 34 and the upper part 36. The cavity 37 is liquid tight and receives liquid from a tube 152 mounted exterior of the housing 31 on top of the upper part 36. The distal extremity of the tube 152 is placed in communication with a port 153 provided in the upper part 36 and through which liquid can be introduced under pressure into the cavity 37 and then withdrawn from the cavity 37 by aspiration or suction through a port 154 also provided in the upper part 37 and in communication with an aspiration tube 156 also mounted on the exterior surface of the upper part 37. Thus it can be seen that a temperature stabilization liquid can be introduced through the tube 152 into the cavity 37 and withdrawn through the aspiration port 154 and the tube 156. The tubes 152 and 156 extend proximally and enter the upper part 36 of the housing in the handle portion 31a and exit therefrom and are connected respectively to the liquid supply 24 and the vacuum supply 26 as shown in FIG. 1.

The entrance port 153 and exit port 154 are provided substantially equidistant longitudinally between the opposite ends of the cavity 37 formed in the tongue depression portion 31c and the upstanding pins 122 form a labyrinth for liquid flow. The flow as shown by arrows 158 is from the entrance port 153 longitudinally of the tongue depression portion 31c traveling in opposite directions toward the distal extremity in one direction and towards the proximal extremity in the one direction and then crossing over to the other side and traveling distally and proximally respectively to the exit suction port 154 to provide a substantially even flow over the bottom surface of the lower part 34 to provide the desired surface temperature stabilization for the exterior of the lower part 36 placed in contact with the body tissue.

Operation and use of the apparatus 21 may now be basically described as follows. Let it be assumed that it is desired to utilize the device 22 for treatment of the tongue to alleviate snoring problems of the patient. The physician typically will examine the patient who for this procedure typically is sitting up permitting the physician easily to view the area where the procedure is to be performed on the tongue. The physician then sets up the RF power supply 23 to set the maximum RF power, the time to be utilized and the maximum temperature for the procedure. Typically a local anaesthetic is applied by the use of a syringe needle so that within two to five minutes the tongue begins to become numb.

The device 22 is removed from its sterile pouch and plugged into the RF power supply and controller 23. The power generator controller 23 is then examined to ascertain that everything is working properly. As soon as the device 22 is ready to be used, the physician grasps the tip of the tongue and holds it in place while advancing the tongue depressor portion 31c of the housing 31 into engagement with the lowermost portion of the tongue equidistant between the sides of the tongue and utilizes the hand grasping the device to depress the lower part 36 of the housing 31 into engagement with the tongue so that it acts as a tongue depressor. As soon as the device is firmly placed, the physician while holding the handle portion 31a in the palm of the hand and with the forefinger grasping the indentation 31b uses the thumb of the same finger to engage the ring 52 and utilizes the thumb to push the ring 52 distally. This causes the T-shaped bar 58 to move the carrier block 63 distally carrying with it the sleeve casings 111 having the needle assemblies 76 affixed therein and causing needle assemblies 76 to advance through the guide tubes 116, 117 and 118 so that the needles 77 and the insulating sleeves 78 carried thereby are advanced in the guide tubes 116, 117 and 118 to cause the sharpened tips 81 of the needle assemblies 76 to advance out of the holes 126, 127 and 128 and to advance in a direction generally perpendicular to the outer surface of the lower part 36 and to penetrate into the tongue. The movement is continued until the needle assemblies have been advanced a suitable distance as for example 20 $\mu$m through the tongue so that the distal extremities of the insulating sleeve 78 extend through the tongue for a distance 10–15 $\mu$m and so that the active region 77a of the needle extends for a distance in the range from 5–10 $\mu$m into the tissue of the tongue. As soon as the three needle assemblies 76 have been deployed in this manner into the tissue of the tongue, radio frequency energy is supplied from the RF power supply to the needle assemblies either automatically or manually under the control of the physician for a suitable period of time ranging from 3–10 minutes and preferably approximately 5 minutes with approximately 10–50 watts of power being applied to each needle at a frequency of 580 kHz.

During this procedure, the patient's teeth can bite down on the bite pads 38 and 39 to help stabilize the device 22 and to maintain its tongue depression portion 31c in engagement with the tongue.

Temperatures occurring during the procedure are carefully monitored. As hereinbefore explained there are three sets of thermocouples with the first thermocouple measuring the temperature at the tip 81 of the needle 77, the second thermocouple measuring the temperature at the distal extremity of the insulating sleeve 78 and the third thermocouple measuring the temperature of the surface of the tongue in contact with the device 22 in the immediate vicinity of the needle 77.

When it is desired to stabilize the temperature of the surface of the tongue in engagement with the device 22, liquid can be-supplied through the liquid supply tube 152 from the liquid supply 24. Thus for example if it is desired to cool the surface of the tongue, chilled liquid as for example a liquid having a temperature as for example from 5° C. to a body temperature of 37° C. can be supplied into the cavity 151 to circulate within the cavity and to be aspirated through the aspiration port 154 into the vacuum supply 26. This liquid supply can be continued as long as desired during the procedure, the temperatures being measured by the thermocouples being closely monitored so as to achieve optimum results from the RF ablation which is being created about the active area 77a of each of the needles 77. Typically this is accomplished at a depth of 10–15$\mu$m from the surface of the tongue so that the surface of the tongue remains substantially undamaged while that region below the surface of the tongue and surrounding the active area 77a is ablated with radio frequency energy. This can be accomplished with little discomfort to the patient particularly when surface temperature stabilization is provided at the surface of the tongue.

By surface temperature stabilization it should be appreciated that in addition to cooling to be provided, heat may be provided if desired by supplying a warmed liquid into the cavity 151. Even though plastic may be utilized for forming the housing 31, it is sufficiently thin so that the plastic will still transmit the fluid temperature to the surface of the tongue to stabilize the temperature at the surface of the tongue during the time that the RF ablation procedure is taking place. By utilizing such a temperature stabilization it is possible to control the temperature at the surface of the tongue keeping cell death substantially below the mucosal layer of the tongue as for example the 10–15 μm hereinbefore described.

The supply of the liquid from the liquid supply 24 can be terminated at any time during the procedure and typically at the end of the procedure immediately after the application of radio frequency energy is terminated. The needle assemblies 76 can then be retracted by having the thumb grasp the ring 52 and pulling it proximally until the distal extremities of the needles 77 are retracted within the guide tubes 116, 117 and 118. As soon as this has been accomplished, the device 22 can be removed from the mouth. Alternatively if desired, the device can again be utilized in creating additional lesions within the tongue of the patient by merely shifting the tongue depressor portion 31c sideways in one direction or the other and then advancing the needles 77 again into the tissue of the tongue by forwardly advancing the ring 52. Radio frequency energy and the application of a temperature stabilization liquid can be applied to the device to perform a similar procedure and after termination, the ring 52 can be withdrawn to retract the needle assemblies 76 into the guide tubes 116, 117 and 118. If desired, the same procedure can be performed in another area of the tongue until the desired radio frequency ablation has been accomplished. The device can then be removed from the tongue of the patient and the patient can be permitted to leave. Typically such a procedure can be accomplished in an out patient clinic.

If it is desirable to eliminate the liquid for obtaining surface temperature stabilization, electrical means in the form of a Peltier device 161 such as shown in FIG. 9 can be adhered to the inner surface of the lower part 36 of the housing 31 by a suitable means such as an adhesive. Such a Peltier device 161 can be provided with conductors for supplying electrical energy to the same which are connected through the cable 106 to the RF power supply and controller 23. As is well known to those skilled in the art, the Peltier device 161 can be utilized to provide cooling and heating as desired by controlling the application of electrical energy to the same. In order to accommodate the guide tubes 116, 117 and 118, the Peltier device can be provided with holes 162 extending through the same in registration with the holes 126, 127 and 128.

Another embodiment of a tissue ablation apparatus incorporating the present invention is a tissue ablation apparatus 201 as shown in FIG. 10 that consists of a device 202 which is connected to an RF power supply and controller 203 and a light box 204. The device 202 consists of a housing 206 formed of the same plastic as the housing 31. The housing 206 is provided with a handle portion 206a which is adapted to be grasped by the palm of the hand and the three fingers of the hand including the thumb and forefinger. It is provided with an intermediate portion 206b which is provided with an arcuate recess 207 which is adapted to be grasped by the forefinger of the hand holding the handle portion 206a. It is also provided with a probe portion 206c which extends at a suitable angle as for example 45–90° and preferably approximately 60° with respect to the handle portion 206a.

The housing 206 is formed in two side parts 211 and 212 which are fastened together much in the same way as the lower and upper parts 34 and 36 of the housing 31. Thus as described therein they are also provided with tongue and groove mating portions and with an adhesive to fasten the two parts 211 and 212 together. A slider 216 is slidably mounted on the exterior of the handle portion 206a of the housing 206 and is constructed in the same manner as the slider 51 in the apparatus 21. Thus the slider 216 is provided with a ring 217 adapted to be engaged by the thumb. The ring 217 is provided with a slot 218 which travels over a longitudinally extending protrusion 219 on the housing 206. The slider 216 is provided with depending side arms 221 corresponding to the side arms 56 and 57 of the device 22. The side arms 221 are connected to opposite ends of a T-shaped bar 222 which is connected to a carrier block 223 in the same manner as carrier block 63 is slidably mounted in a sliding guide block assembly 224 of the same type a sliding guide block assembly 66 which is mounted within the housing 206 on posts 226.

A single carrier tube 231 is mounted in the carrier block 223 rather than three carrier tubes 73 of the type hereinbefore described in connection with the device 22. A needle assembly 236 is mounted in the carrier tube 231 and consists of a needle 237 having a two-layer insulating sleeve 238 thereon. The insulating sleeve 238 is formed by polyimide shrink tubing having a thin wall thickness as for example 0.003". The needle assembly 236 is substantially identical to the needle assembly 76 and carries the first and second thermocouples (not shown) with one being disposed at the tip of the needle 237 and the other being disposed in insulating sleeve 238. The insulating sleeve is disposed so that there is provided a bare exposed portion 237a of the needle 237 to provide an active region for RF ablation in the same manner as the portion 77a of the needle 77.

An angled bridge 251 is provided within the housing 206 which extends from the intermediate portion 206b to the probe portion 206c. A guide tube 252 formed of a suitable material such a stainless steel is mounted within the bridge 251 in a suitable manner such as by molding the bridge 251 around the guide tube 252. The guide tube 252 is provided with a bore 253 and has a portion 252 which is in alignment with a bore 254 provided in the portion of the bridge 251 immediately adjacent the sliding guide block assembly 224. It is also provided with a curved intermediate portion 252b which adjoins a straight portion 252c that extends through and beyond the probe portion 206c of the housing 206 as shown particularly in FIG. 10. The needle assembly 236 extends distally from the carrier tube 231 carried by the carrier block 223 and extends into the bore 254 and the bridge 251 and then enters the lumen 253 of the guide tube 252.

By movement of the slider 216 by the thumb of the hand grasping the handle portion 206a of the housing 206, the needle assembly 236 can be moved from a position in which it is retracted within the distal extremity of the guide tube 252 to an outermost extreme deployed position in which the distal extremity of the needle assembly 236 is disposed beyond the distal extremity of the guide tube 252 so that at least 20 μm extends beyond the distal extremity of the guide tube 252 so that 15 μm of the insulation extends beyond the guide tube 252 and the bare insulated portion of the needle ranges from a length of 5–10 μm is adapted to penetrate into the tissue. A connector 256 is mounted on the proximal extremity of the needle assembly 236 and has connected thereto a flexible insulated conductor 257 which extends into a cord 258 for supplying radio frequency energy to the needle 236. The wires connected to the first and second thermocouples are not shown but are connected into the electrical cord 258 and extend to the RF power supply and controller 203 in the same manner as the conductor wires for the first and second thermocouples in the device 22.

A guide sleeve 271 formed of a suitable material such as stainless steel is also mounted in the bridge 251 and is provided with a large bore 272. The bore 272 has a suitable size as for example a diameter of 5 mm. The guide sleeve 271 has a length so that it extends beyond the probe portion 206c of the housing 206 by a suitable distance as for example approximately 2". A fitting 276 is provided which has a cylindrical shaft 277 which has an enlarged hub 278 on its proximal extremity. The shaft is provided with a bore 279 which extends through the shaft and opens into the hub 278. The distal extremity of the shaft 277 is provided with an annular recess 281 and is secured by a snap fit into a grommet 282 mounted in the probe portion 206c of the housing 206. When the adapter 276 is snapped into place, its bore 279 is in alignment with the bore provided in the guide sleeve 271. The adapter 276 is adapted to receive a fiber optic light scope of a conventional type which is adapted to be seated within the hub 278 of the adapter 276 so that a cylindrical fiber optic light pipe 287 extends through the guide sleeve 271 and extends distally therefrom to a region which is just proximal of the distal extremity of the guide tube 252 so that tissue being penetrated by the needle assembly 236 can be observed by the physician. The light scope 286 is provided with a fitting 288 which is connected to a conventional light source as for example the light box 204 shown in FIG. 10. The scope is also provided with an eye piece 289 permitting the physician to place his eye against the eye piece 289 to view the procedure being performed while the physician is holding the device 202 in his hand.

Operation and use of the apparatus 201 is very similar to operation and use of the apparatus 21 hereinbefore described. However, rather than there being a three-needle device as in the apparatus 22, the device 202 is a single-needle device. Typically, the device 202 can be utilized for creating lesions by RF ablation in soft tissue in the upper airway, such as in the turbinates, uvula, soft palate and the like. As in the previously described procedure, a local anaesthetic is administered to the soft tissue to be treated and a grounding electrode is placed on an appropriate location on the patient. The physician removes the device 202 from its sterile pouch and then plugs it into the RF power supply and controller 203. The RF power supply and controller 203 is then set up to perform the desired procedure. The physician while grasping the handle portion 206a by the palm of the hand and three fingers of the hand and with the index finger inserted in the recess 207 places the distal extremity of the guide tube 252 against the tissue to be treated as for example a turbinate with the needle assembly 236 in the nondeployed position. The physician slowly deploys the needle 237 by using the thumb to push the ring 217 upwardly and to move the needle assembly 236 out of the guide tube 252 and into the tissue. As this is occurring, the physician observes the impedance being registered by the controller 203 and continues advancing the needle assembly until a low impedance is reached thereby ascertaining that good conductivity is established between the grounding electrode and the RF electrode. As soon as the needle assembly 236 has been deployed sufficiently so that the insulation extends 10–15 μm below the mucosal surface and so that the active area of the needle extends another 5–10 μm into the tissue, radio frequency energy is applied to start the ablation procedure. The ablation procedure is continuously monitored by measuring impedance and also by measuring the temperatures encountered by the first and second thermocouples. During the time that this procedure is taking place, the physician can observe the procedure by placing his eye against the eye piece 289. The physician typically observes the tissue while the radio frequency ablation is taking place to ascertain whether or not there is any edema or discoloration taking place at the surface level of the tissue. Typically the radio frequency energy can be applied by the operation of a foot operated switch. The turbinate ablation procedure typically takes a relatively short time as for example a minute to a minute and a half. During this time, the temperature rise from the body temperature to the set temperature which typically is between 80 and 90° C. takes place within a matter of 30 seconds. The algorithm in the radio frequency power supply and controller will stabilize the temperature at a set temperature for the duration of the procedure. The radio frequency generator and controller 203 automatically terminates the application of the radio frequency generator as determined by the algorithm. The physician can then retract the needle assembly 236 by pulling proximally on the ring 217 with the thumb of the hand in which the device can be disposed of after removal of the light scope 286.

It should be appreciated that it may be desirable to utilize the device 202 for performing other RF ablation procedures on the turbinates of the same patient in other locations utilizing the same procedures hereinbefore described. Similarly, the device can also be utilized for performing an ablation procedure on the uvula of the patient. However, typically it is desired to utilize the device 202 with a bent guide tube 252. This can be accomplished by bending the guide tube through an angle of 45–70° with respect to the probe portion 206c. This can be readily accomplished by use of a bending tool disclosed in co-pending application Ser. No. 08/941,403 filed Sep. 30, 1997 (A-64860) Typically the uvula is treated by inserting the needle assembly into a region which is above the depending portion of the uvula. This procedure can be aided by using a modified device as shown in FIG. 11 in which an L-shaped member 291 is secured to the distal extremity of the guide sleeve 271 to provide an abutment member which is disposed distally of the guide tube 252, as for example one-half inch, so that there is room for the uvula to be inserted into the space between the member 291 and the distal extremity of the guide tube 252. In this way, the member 291 can serve as an anvil and to hold the very floppy tissue of the uvula while the needle 237 and the insulating sleeve 238 are advanced into the uvula and the radio frequency ablation is performed in the manner hereinbefore described. The needle assembly 236 can be removed after the ablation procedure has been completed, after which the L-shaped member 291 can be removed from behind the uvula and the device removed from the mouth of the patient.

When the lesion is formed in this manner, the resorption of tissue will cause the depending portion to be pulled upwardly.

From the foregoing it can be seen that there has been provided a tissue ablation apparatus and a method for performing the same which is advantageous for invasive treatment of disorders of the upper airway by the radio frequency ablation of soft tissues in the upper airway. The device is constructed in such a manner so that a light pipe can be provided to improve visualization of the procedure. The device is constructed in such a manner so that it can be utilized by either right handed or left handed physicians since the sliding knob can be grasped by the thumb of either hand holding the device.

What is claimed:

1. A tissue ablation apparatus for minimally invasive treatment for disorders of the upper airway by the treatment of soft tissues in the upper airway comprising a hand-held device adapted to be held by the human hand, means for delivering radio frequency energy to the hand-held device, the hand-held device comprising a housing having a handle portion adapted to be grapsed by the human hand and a probe portion, at least one guide tube mounted in the probe portion and having a bore extending therethrough, a carrier block slidably mounted in the housing relative to the guide tube, a needle assembly mounted in the carrier block assembly movable with the carrier block assembly, the needle assembly extending distally of the carrier block and being slidably disposed in the at least one guide tube, a slider mounted on the housing exterior of the housing for slidable movement longitudinally of the housing and adapted to be grasped by the thumb of the hand holding the housing and means connecting the slider to the carrier block whereby when the slider is moved distally, the carrier block with the needle assembly is moved in the guide tube distally of the guide tube for entrance into the soft tissue.

2. A tissue ablation apparatus as in claim 1 wherein first and second guide tubes are provided and are mounted in the probe portion of the housing and having bores extending therethrough and first and second needle assemblies mounted in the carrier block and slidably disposed respectively in the first and second guide tubes.

3. A tissue ablation apparatus as in claim 2 wherein the soft tissue is the tongue and wherein said probe portion is provided with an elongate planar tongue depressor portion adapted to engage the tongue and having first and second longitudinally spaced-apart holes therein and wherein said first and second guide tubes have distal extremities mounted in the holes, the first and second guide tubes having proximal extremities lying in a horizontal plane and having the distal extremities lying in a vertical plane extending at right angles to the proximal extremities laying in a horizontal plane.

4. A tissue ablation apparatus as in claim 2 further including temperature sensing means coupled to the first and second needle assemblies and to the means for delivering radio frequency energy, additional temperature sensing means mounted in the probe portion adjacent the holes through which the first and second guide tubes extend.

5. A tissue ablation apparatus as in claim 4 further comprising means coupled to the tongue depressor portion for stabilizing the temperature at the surface of the tongue depressor portion engaging the tongue and under the control of the additional temperature sensing means.

6. A tissue ablation apparatus as in claim 5 wherein said means for stabilizing the temperature includes a probe portion having a cavity therein in contact with the tongue depressor portion and means for supplying a liquid to the cavity and withdrawing the liquid from the cavity.

7. A tissue ablation apparatus as in claim 6 wherein said liquid is a cooling liquid.

8. A tissue ablation apparatus as in claim 6 wherein said liquid is a heating liquid.

9. A tissue ablation apparatus as in claim 5 wherein said means for stabilizing the temperature includes a Peltier device mounted in the probe portion in contact with the tongue depressor portion.

10. A tissue ablation apparatus as in claim 1 wherein first and second and third guide tubes are provided and are mounted in the probe portion of the housing and having bores extending therethrough and first and second and third needle assemblies mounted in the carrier block and slidably disposed respectively in the first, second and third guide tubes.

11. A tissue ablation apparatus as in claim 1 together with temperature sensing means carried by the at least one needle assembly having a needle and an insulating sleeve and including a first temperature sensor carried by the needle and a second temperature sensor carried by the insulating sleeve.

12. A tissue ablation apparatus as in claim 1 wherein said handle portion is inclined at an angle with respect to the probe portion.

13. A tissue ablation apparatus as in claim 1 together with a bridge member mounted in the housing, said bridge member having at least one guide tube disposed therein, a guide sleeve carried by the bridge member and disposed parallel to the at least one guide tube and a light scope removably mounted in the guide tube permitting the physician to view the soft tissue as the needle assembly is advanced into the soft tissue.

14. A method for minimally invasive treatment of the treatment of soft tissues in the upper airway of a patient by the treatment of soft tissues in the airway by the use of a hand-held device adapted to be held by the human hand and having a needle assembly movably carried thereby and with the needle assembly comprising a needle and an insulating layer carried by the needle, means for delivering radio frequency energy to the hand-held device, comprising advancing the hand-held device to that it is in proximity to the soft tissue to be treated, advancing the needle into the soft tissue for a distance of approximately 10 microns and wherein the needle extends free of the insulating layer for a distance of 5–10$\mu$ in the tissue and supplying radio frequency energy to the needle assembly to cause ablation of the tissue and withdrawing the needle assembly from the tissue after it has been treated and removing the hand-held device from the soft tissue.

15. A method as in claim 14 together with the step of supplying light to the tissue to be treated and observing the tissue while it is being treated.

16. A method as in claim 14 together with the step of treating the uvula by retaining the uvula with the hand-held device during the time that the needle assembly is being advanced into the uvula.

* * * * *